(12) United States Patent
Chang et al.

(10) Patent No.: US 9,103,750 B2
(45) Date of Patent: Aug. 11, 2015

(54) APPARATUS AND METHOD FOR SAMPLING UNDERWATER RADIOACTIVE SOLUTION

(71) Applicants: Kuo-Yuan Chang, Taoyuan County (TW); Tsu-Han Cheng, Taoyuan County (TW)

(72) Inventors: Kuo-Yuan Chang, Taoyuan County (TW); Tsu-Han Cheng, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 272 days.

(21) Appl. No.: 13/679,237

(22) Filed: Nov. 16, 2012

(65) Prior Publication Data

US 2013/0167668 A1    Jul. 4, 2013

Related U.S. Application Data

(63) Continuation-in-part of application No. 12/842,615, filed on Jul. 23, 2010, now abandoned.

(30) Foreign Application Priority Data

Jun. 8, 2010   (TW) .............................. 99118518 A

(51) Int. Cl.
| | |
|---|---|
| *G01N 1/14* | (2006.01) |
| *G21D 1/02* | (2006.01) |
| *G21F 7/06* | (2006.01) |
| *G01N 1/10* | (2006.01) |

(52) U.S. Cl.
CPC .. *G01N 1/14* (2013.01); *G21D 1/02* (2013.01); *G21F 7/068* (2013.01); *G01N 2001/1037* (2013.01); *G01N 2001/1427* (2013.01); *Y02E 30/40* (2013.01)

(58) Field of Classification Search
CPC .......... G01N 1/14; G01N 1/24; G01N 1/2273
USPC ...................................................... 73/864.34
See application file for complete search history.

(56) References Cited

U.S. PATENT DOCUMENTS

| | | | | | |
|---|---|---|---|---|---|
| 3,298,398 | A | * | 1/1967 | Smith ............................ | 138/94 |
| 5,533,407 | A | * | 7/1996 | Besnier ...................... | 73/864.25 |
| 7,441,472 | B2 | * | 10/2008 | Vinton ....................... | 73/864.62 |

* cited by examiner

*Primary Examiner* — Hezron E Williams
*Assistant Examiner* — Rodney T Frank
(74) *Attorney, Agent, or Firm* — Locke Lord LLP; Tim Tingkang Xia, Esq.

(57) ABSTRACT

An apparatus and a method for sampling underwater radioactive solution. The apparatus includes a main unit, a connecting rod inserted into the main unit, a connecting ring connected to one side of the connecting rod, a container unit connected to the opposite side of the connecting ring, a solution access channel, an air motor for changing air pressure in the container unit to draw or extract the radioactive solution in or out of the container unit, a holder for fixing the air motor on the main unit, a synchronizing connector for connecting the connecting rod to the air motor, so as to synchronize the back-and-forth movement of the connecting rod with the air pressure of the air motor, a control unit for controlling the operation of the air motor, a flexible pipe connecting the air motor to the control unit, and a depth-setting unit.

6 Claims, 4 Drawing Sheets

APPARATUS AND METHOD FOR SAMPLING UNDERWATER RADIOACTIVE SOLUTION

CROSS-REFERENCE TO RELATED APPLICATIONS

This application is a continuation-in-part of U.S. patent application Ser. No. 12/842,615, filed Jul. 23, 2010, entitled "APPARATUS AND METHOD FOR SAMPLING UNDERWATER RADIOACTIVE SOLUTION", by Kuo-Yuan Chang and Tsu-Han Cheng, which itself claims priority to and the benefit of, pursuant to 35 U.S.C. §119(a), Patent Application No. 099118518 filed in Taiwan, R.O.C. on Jun. 8, 2010, entitled "APPARATUS AND METHOD FOR SAMPLING UNDERWATER RADIOACTIVE SOLUTION", by Kuo-Yuan Chang and Tsu-Han Cheng, the entire contents of which are hereby incorporated by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

TECHNICAL FIELD

The present disclosure relates to a sampling apparatus and method, and more particularly, to a sampling apparatus and method for underwater radioactive solution.

BACKGROUND OF THE INVENTION

Usually the radioactive waste of a nuclear facility is stored in the radioactive reservoir or in the container of the reservoir. To resist high-dosage radiation of the radioactive waste, the radioactive waste is distributed in reservoirs and/or their containers with water filled in. Due to considerations of nuclear security and protection, it is in need to sample, analyze, and monitor the radioactive solution in the reservoirs and their containers, in order to determine the nuclides and the radiation dosage at different depths in the radioactive solution wherein. Thus a database concerning the radioactive conditions can be built up to facilitate the setup of a standard operating procedure for nuclear facilities.

Conventional sampling techniques for underwater radioactive solution are generally applicable to the shallow part of the reservoirs or their containers, and are not capable to sample the solution in the deep. Besides, radiation dosage would accumulate in human bodies of samplers or operators, who have to work in the radioactive circumstance for a long time. More recently a remote-controlled sampling apparatus for underwater radioactive solution was proposed. However, complex operation and an additional underwater camera are prerequisite for the apparatus.

Accordingly, there remains a need in the art for an apparatus and/or a method for sampling underwater radioactive solution that is more effective, low-cost, easy to process, and radiation-resistant than the presently available.

SUMMARY OF THE INVENTION

According to one aspect of the present invention, the embodiment provides a sampling apparatus for underwater radioactive solution, comprising: a main unit; a connecting rod, inserted into the main unit; a connecting ring, connected to one side of the connecting rod; a container unit, connected to the opposite side of the connecting ring; a solution access channel, as a pathway for the radioactive solution to be drawn in or extracted out of the container unit; a motor having a piston, for changing air pressure in the container unit to draw or extract the radioactive solution in or out of the container unit; a holder, for fixing the motor on the main unit; a synchronizing connector, for connecting the connecting rod to the piston of the motor, so as to synchronize the back-and-forth movement of the connecting rod with the air pressure of the motor; a control unit, for controlling the operation of the motor and then the sampling operation for the radioactive solution; flexible pipes, connecting the motor to the control unit, so as to provide or release air in the air compressor; and a depth-setting unit, disposed on outer walls of the main unit to set an underwater depth for the sampling apparatus to sample the radioactive solution.

According to another aspect of the present invention, the embodiment provides a sampling method for underwater radioactive solution, comprising: providing a sampling apparatus for underwater radioactive solution; setting an underwater depth for the depth-setting unit; putting the sampling apparatus in the radioactive reservoir of nuclear facilities or in the container of said reservoir at the underwater depth; controlling the operation of the piston of the motor with the control unit and thus move the connecting rod backward to draw in the solution sample; taking the sampling apparatus out of the radioactive reservoir or the container; and controlling the operation of the piston of the motor with the control unit and thus move the connecting rod forward to extract the solution sample out.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure.

DESCRIPTION OF THE EXEMPLARY EMBODIMENTS

For further understanding and recognizing the fulfilled functions and structural characteristics of the disclosure, several exemplary embodiments cooperating with detailed description are presented as follows.

Figure 1:
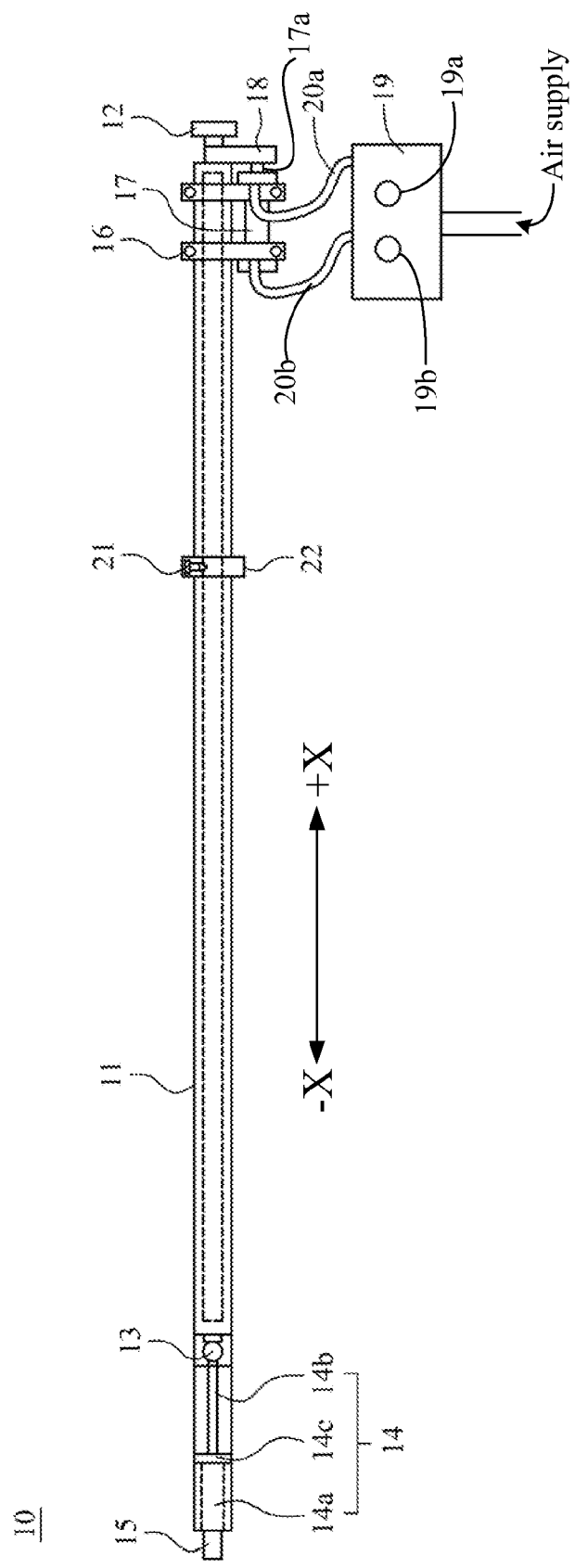
FIG. 1 is a schematic diagram showing the structure of an apparatus for sampling underwater radioactive solution, according to an embodiment of the invention.

Please refer to FIG. 1, which is a schematic diagram showing the structure of an apparatus for sampling underwater radioactive solution, according to an embodiment of the invention. The apparatus is used for sampling underwater radioactive waste stored in the radioactive reservoir of nuclear facilities or in the container of said reservoir in order to determine the nuclides and the radiation dosage at different depths in the radioactive solution. In FIG. 1, the sampling apparatus 10 comprises a main unit 11, a connecting rod 12, a connecting ring 13, a container unit 14, a solution access channel 15, a holder 16, a motor 17, a synchronizing connector 18, a control unit 19, flexible pipes 20a and 20b, and a depth-setting unit 21. Generally the main unit 11 has a sufficient length to prevent a sampler or operator from approaching the radioactive waste and its radiation dosage. Also the main unit 11 has a depth scale on itself to facilitate setting the depth to sample the radioactive solution. The connecting rod 12 is inserted into the main unit 11 and is connected to one side of the connecting ring 13. The opposite side of the connecting ring 13 is connected to the container unit 14. The solution access channel 15 is used as a pathway for the radioactive solution to be drawn in or extracted out of the container unit 14. The motor 17 contains a piston 17a. The motor 17 is used to change air pressure in the container unit 14, so as to draw in or extract out the radioactive solution sample in the container unit 14. The holder 16 is used to fix the motor 17 on the main unit 11. The synchronizing connector 18 is used to connect the connecting rod 12 to the piston 17a of the motor 17, so as to synchronize the back-and-forth movement of the connecting rod 12 with the air pressure of the motor 17. The control unit 19 has a +X button 19a and a −X button 19b. The control unit 19 is used to control the operation of the motor 17 and then the sampling operation for the radioactive solution. The flexible pipes 20a and 20b are used to connect the motor 17 to the control unit 19, so as to provide or release air in the motor 17. When the +X button 19a is pressed, the control unit 19 adjusts the air pressure of the motor 17 through the flexible pipes 20a and 20b. The change of the air pressure in the motor 17 drives the piston 17a of the motor 17 to move along +X direction. The movement of the piston 17a then drives the connecting rod 12 to move along the +X direction through the synchronizing connector 18. When the −X button 19b is pressed, the control unit 19 adjusts the air pressure of the motor 17 through the flexible pipes 20a and 20b. The change of the air pressure in the motor 17 drives the piston 17a of the motor 17 to move along −X direction. The movement of the piston 17a then drives the connecting rod 12 to move along the −X direction through the synchronizing connector 18. The depth-setting unit 21 is disposed on outer walls of the main unit 11 and is used to set an underwater depth for the sampling apparatus 10 to sample the radioactive solution. When sampling the radioactive solution in a container of the radioactive reservoir in a nuclear facility, the depth-setting unit 21 further comprises a fixer 22 to fix the main unit 11 on the container and outside the entry of the container.

Figure 2:
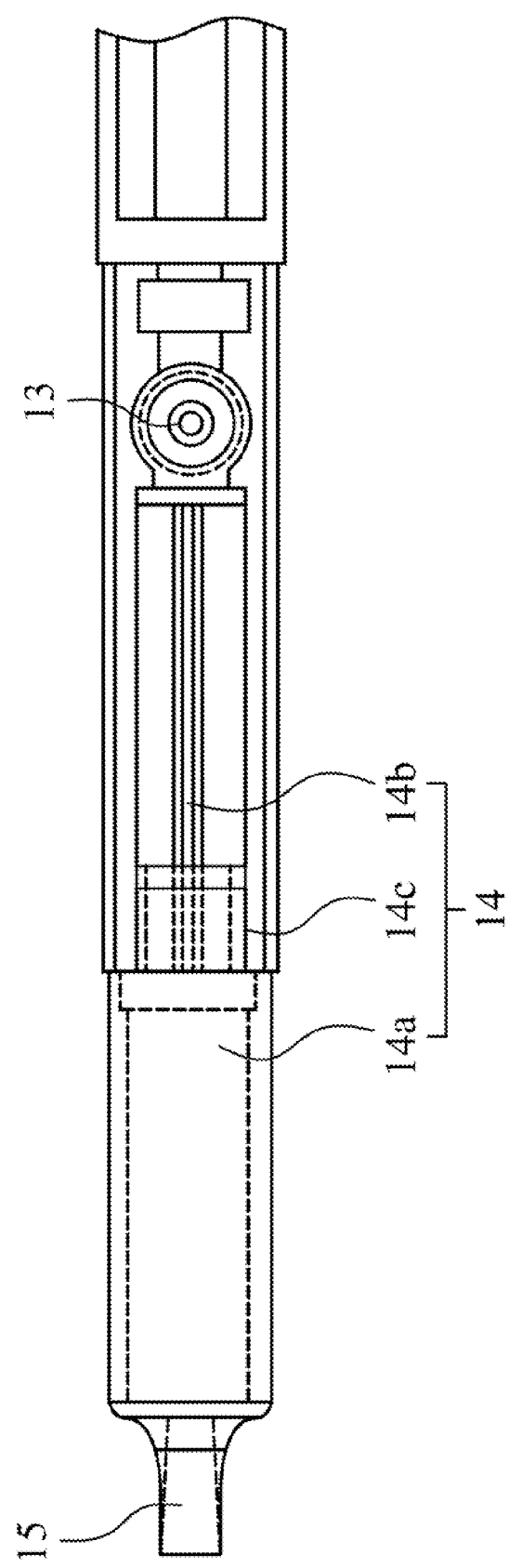
FIG. 2 is a more detailed schematic structure of the container unit in the sampling apparatus.

FIG. 2 schematically illustrates a more detail structure of the container unit 14 in the sampling apparatus 10. The container unit 14 further comprises a solution container 14a, an adjusting rod 14b, and a ring buckle 14c. The solution container 14a is used to store the drawn-in solution sample. The adjusting rod 14b is used to adjust the draw-in or extracted-out volume of the sampled solution in the solution container 14a. The ring buckle 14c is used to fix or take apart the solution container 14a on or from the main unit 11. The solution container 14a should be taken apart form the main unit 11 once a sampling process is done, and be replaced with a new one to prevent contamination from residues of the sampled solution.

Figure 3:
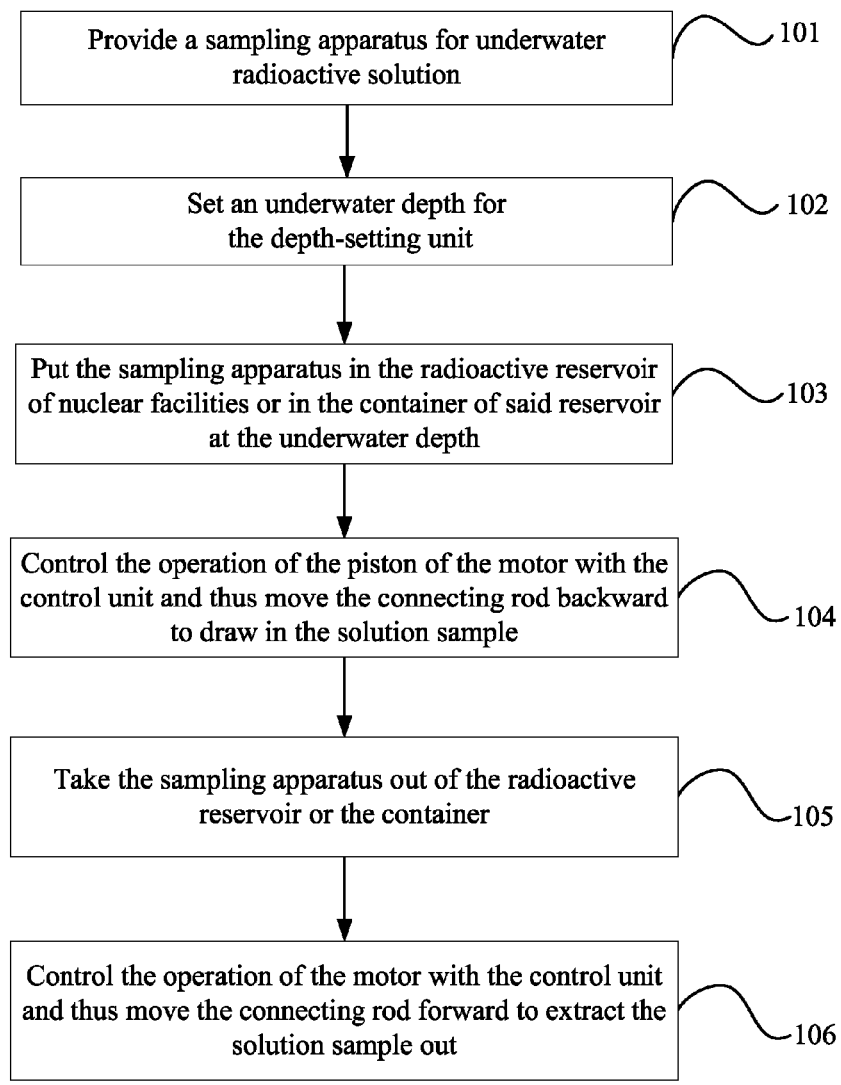
FIG. 3 is a flowchart of a method for sampling underwater radioactive solution, according to another embodiment of the invention.
Figure 4:
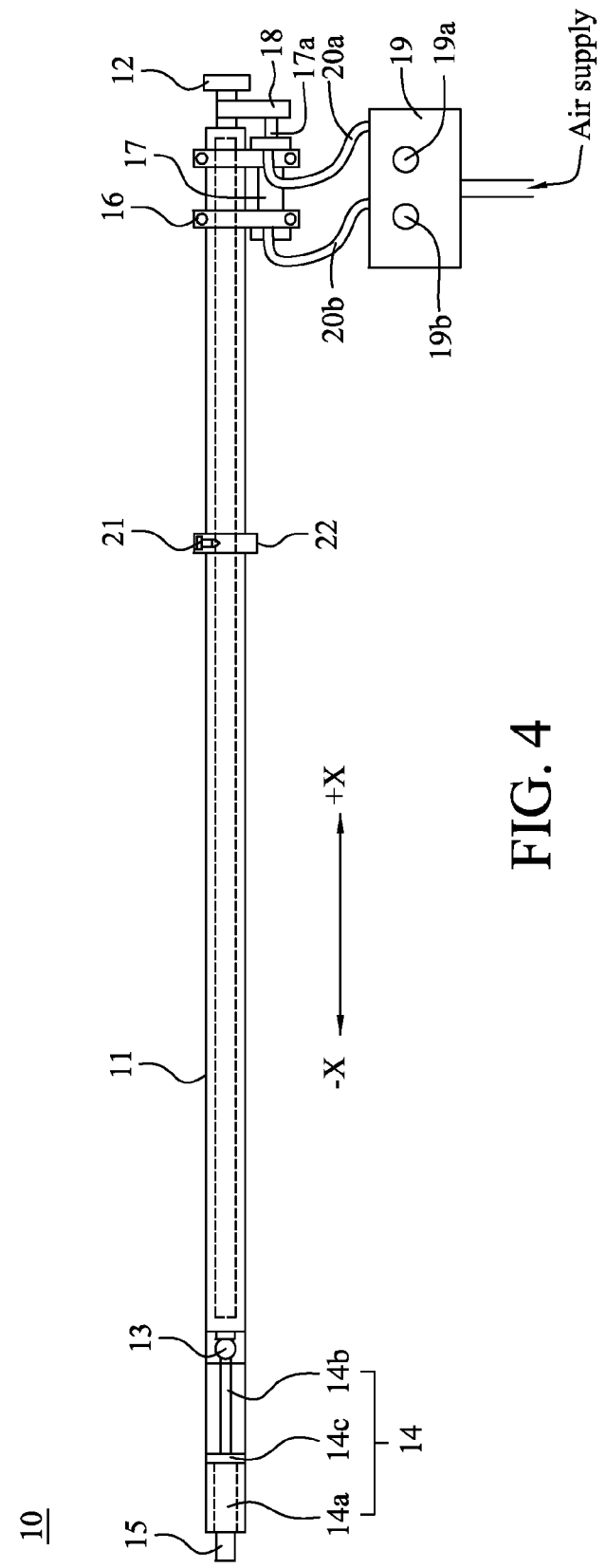
FIG. 4 is indicative at least of the situation in which when the −X button 19b is pressed.

FIG. 3 schematically shows a flowchart of a method for sampling underwater radioactive solution, according to another embodiment of the invention. The sampling method comprises the following steps, wherein the sampling apparatus 10 has been shown in FIG. 1 and the foregoing descriptions. Step 101 is to provide a sampling apparatus 10 for underwater radioactive solution, comprising a main unit 11, a connecting rod 12, a connecting ring 13, a container unit 14, a solution access channel 15, a holder 16, a motor 17, a synchronizing connector 18, a control unit 19, flexible pipes 20a and 20b, and a depth-setting unit 21, wherein the depth-setting unit 21 is disposed on outer walls of the main unit 11, the control unit 19 having buttons 19a and 19b and is used to control the operation of the motor 17, and the synchronizing connector 18 is used to connect the connecting rod 12 to a piston 17a of the motor 17, so as to synchronize the back-and-forth movement of the connecting rod 12 with the air pressure of the motor 17. Step 102 is to set an underwater depth for the depth-setting unit 21. Step 103 is to put the sampling apparatus 10 in the radioactive reservoir of nuclear facilities or in the container of said reservoir at the underwater depth. Step 104 is to control the operation of the motor 17 with the control unit 19 and thus move the connecting rod 12 backward (along +X direction) to draw in the solution sample. Step 105 is to take the sampling apparatus 10 out of the radioactive reservoir or the container. And finally step 106 is to control the operation of the motor 17 with the control unit 19 and thus move the connecting rod 12 forward (along −X direction) to extract the solution sample out.

Preferably in the step 101 of the embodiment, the container unit 14 may further comprises a solution container 14a, an adjusting rod 14b, and a ring buckle 14c. The solution container 14a is used to store the drawn-in solution sample. The adjusting rod 14b is used to adjust the draw-in or extracted-out volume of the sampled solution in the solution container 14a. The ring buckle 14c is used to fix or take apart the solution container 14a on or from the main unit 11.

Furthermore in the step 101 of the embodiment, the depth-setting unit 21 further comprises a fixer 22, to fix the main unit 11 on the container and outside the entry of the container of the radioactive reservoir in a nuclear facility to be sampled.

It is noted that the control unit 19 in the sampling apparatus 10 can be a motor, so as to control the operation of the piston 17a of the motor 17. Meanwhile the synchronizing connector 18 is used to connect the connecting rod 12 with the piston 17a of the motor 17, so as to synchronize the back-and-forth movement of the connecting rod 12 with the air pressure of the motor 17, to control drawing or extracting the radioactive solution sample in or out of the container unit 14.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A sampling apparatus for underwater radioactive solution, comprising:
   a main unit;
   a connecting rod, inserted into the main unit;
   a connecting ring, connected to one side of the connecting rod;

a container unit, connected to the opposite side of the connecting ring;

a solution access channel, as a pathway for the radioactive solution to be drawn in or extracted out of the container unit;

a motor having a piston, for changing air pressure in the container unit to draw or extract the radioactive solution in or out of the container unit;

a holder, for fixing the motor on the main unit;

a synchronizing connector, for connecting the connecting rod to the piston of the motor, so as to synchronize the back-and-forth movement of the connecting rod with the air pressure of the motor;

a control unit, for controlling the operation of the piston of the motor and then the sampling operation for the radioactive solution;

flexible pipes, connecting the motor to the control unit, so as to provide or release air in the motor; and a depth-setting unit, disposed on outer walls of the main unit to set an underwater depth for the sampling apparatus to sample the radioactive solution.

2. The sampling apparatus of claim 1, wherein the container unit further comprises:

a solution container; and an adjusting rod, for adjusting the draw-in or extracted-out volume of the sampled solution in the solution container.

3. The sampling apparatus of claim 1, when sampling the radioactive solution in a container of the radioactive reservoir in a nuclear facility, the depth-setting unit further comprising a fixer to fix the main unit on the container and outside the entry of the container.

4. A sampling method for underwater radioactive solution, comprising the steps of:

providing a sampling apparatus for underwater radioactive solution, the sampling apparatus comprising a main unit, a connecting rod, a connecting ring, a container unit, a solution access channel, a motor having a piston, a holder, a synchronizing connector, a control unit, flexible pipes, and a depth-setting unit, wherein the depth-setting unit is disposed on outer walls of the main unit, the control unit is used to control the operation of the piston of the motor, and the synchronizing connector is used to connect the connecting rod to the piston of the motor, so as to synchronize the back-and-forth movement of the connecting rod with the air pressure of the motor;

setting an underwater depth for the depth-setting unit;

putting the sampling apparatus in a radioactive reservoir of nuclear facilities or in the container of said reservoir at the underwater depth;

controlling the operation of the piston of the motor with the control unit and thus move the connecting rod backward to draw in the solution sample;

taking the sampling apparatus out of the radioactive reservoir or the container; and controlling the operation of the piston of the motor with the control unit and thus move the connecting rod forward to extract the solution sample out.

5. The sampling method of claim 4, wherein the container unit further comprises:

a solution container; and an adjusting rod, for adjusting the draw-in or extracted-out volume of the sampled solution in the solution container.

6. The sampling method of claim 4, when sampling the radioactive solution in a container of the radioactive reservoir in a nuclear facility, the depth-setting unit further comprising a fixer to fix the main unit on the container and outside the entry of the container.

\* \* \* \* \*